United States Patent
Fukuoka et al.

(10) Patent No.: US 10,479,799 B2
(45) Date of Patent: *Nov. 19, 2019

(54) SOLID CATALYST FOR DEHYDRATION OF MANNITOL, AND METHOD FOR PRODUCING 2, 5-SORBITAN AND/OR ISOMANNIDE USING THIS CATALYST

(71) Applicants: NATIONAL UNIVERSITY CORPORATION HOKKAIDO UNIVERSITY, Hokkaido (JP); CLARIANT CATALYSTS (JAPAN) K.K., Tokyo (JP)

(72) Inventors: Atsushi Fukuoka, Hokkaido (JP); Hirokazu Kobayashi, Hokkaido (JP); Xin Chen, Toyama (JP)

(73) Assignees: NATIONAL UNIVERSITY CORPORATION HOKKAIDO UNIVERSITY, Hokkaido (JP); CLARIANT CATALYSTS (JAPAN) K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/322,351

(22) PCT Filed: Jul. 20, 2017

(86) PCT No.: PCT/JP2017/026288
§ 371 (c)(1),
(2) Date: Jan. 31, 2019

(87) PCT Pub. No.: WO2018/042932
PCT Pub. Date: Mar. 8, 2018

(65) Prior Publication Data
US 2019/0169205 A1    Jun. 6, 2019

(30) Foreign Application Priority Data
Aug. 29, 2016 (JP) .................. 2016-166658

(51) Int. Cl.
*C07D 493/04*    (2006.01)
*C07D 307/20*    (2006.01)
*C07B 61/00*    (2006.01)
*B01J 29/08*    (2006.01)
*B01J 29/70*    (2006.01)

(52) U.S. Cl.
CPC .......... *C07D 493/04* (2013.01); *B01J 29/082* (2013.01); *B01J 29/084* (2013.01); *B01J 29/7007* (2013.01); *C07B 61/00* (2013.01)

(58) Field of Classification Search
CPC ........................... C07D 493/04; C07D 307/20
USPC .................................... 549/464, 476
See application file for complete search history.

(56) References Cited

U.S. PATENT DOCUMENTS

| | | | |
|---|---|---|---|
| 4,408,061 A | 10/1983 | Salzburg et al. | |
| 6,013,812 A | 1/2000 | Haas et al. | |
| 6,689,892 B2 | 2/2004 | Andrews et al. | |
| 9,630,974 B2 | 4/2017 | Stensrud et al. | |
| 9,920,064 B2 * | 3/2018 | Fukuoka | B01J 29/70 |

FOREIGN PATENT DOCUMENTS

| | | | |
|---|---|---|---|
| JP | 2016-037481 A | 3/2016 | |
| JP | 2016-121143 A | 7/2016 | |
| WO | WO 2016/009607 A1 * | 1/2016 | B01J 29/70 |

OTHER PUBLICATIONS

International Search Report of the International Searching Authority, dated Sep. 19, 2017, with respect to International Application No. PCT/JP2017/026288.
Kurszewska Maria, et al., The solvent-free thermal dehydration of hexitols on zeolites, Carbohydrate Research, Aug. 2002, vol. 337, Issue 13, p. 1261-1268.
Shirai Masayuki, et al., Intramolecular dehydration of mannitol in high-temperature liquid water without acid catalysts, RSC Advances, 2014, vol. 4, p. 45575-45578.

* cited by examiner

*Primary Examiner* — Charanjit Aulakh
(74) *Attorney, Agent, or Firm* — Scott R. Cox

(57) ABSTRACT

Provided is a solid acid catalyst which enables the production of isomannide and/or 2,5-sorbitan from mannitol with high yield and high safety at low cost. The mannitol may be derived from a cellulose and/or a hemicellulose. The solid acid catalyst for dehydration contains an acid type β-zeolite and/or a Y type zeolite.

12 Claims, 3 Drawing Sheets

REACTION OF CONVERSION FROM CELLULOSE OR HEMICELLULOSE INTO ISOMANNIDE OR 2,5-SORBITAN

EXAMPLE 1 (β-ZEOLITE, Si/Al=75, 150°C)

EXAMPLE 2 (β-ZEOLITE, Si/Al=75, 140°C)

EXAMPLE 3 (H-USY ZEOLITE, Si/Al=40, 150°C)

EXAMPLE 4 (H-USY ZEOLITE, Si/Al=40, 140°C)

SOLID CATALYST FOR DEHYDRATION OF MANNITOL, AND METHOD FOR PRODUCING 2, 5-SORBITAN AND/OR ISOMANNIDE USING THIS CATALYST

TECHNICAL FIELD

The present invention relates to a catalyst for producing 2,5-sorbitan and/or isomannide from mannitol and a process for producing 2,5-sorbitan and/or isomannide from mannitol using the catalyst.

BACKGROUND ART

In recent years, the development of chemical reaction processes utilizing plant resources instead of petroleum resources has been actively carried out, with attention also being given to the development and application of novel production processes for sugar alcohols derived from cellulose have been paid attention. One example of an application is a process to obtain a starting material for a useful chemical substance by dehydrating a sugar alcohol. For example, sorbitol or mannitol, each being a sugar alcohol, is obtained by the hydrolysis and hydrogenation of cellulose. Likewise, mannitol can also be obtained by hydrolysis and hydrogenation of hemicellulose that occupies about ¼ of a biomass component (FIG. 1). Alternatively, mannitol can be obtained in a high yield not only from hemicellulose but also from cellulose by adjusting cellulose hydrolysis conditions. When mannitol obtained from biomass in a large amount as above is dehydrated, isomannide (useful as a starting material for functional plastics and pharmaceuticals) and 2,5-sorbitan having wide use applications as an emulsifying agent or a surfactant for food, pharmaceuticals and cosmetics are obtained.

As shown in FIG. 1, although the reaction to obtain 2,5-sorbitan from mannitol proceeds as a one-stage dehydration reaction, the process to obtain isomannide consists of a two-stage dehydration reaction. Since mannitol has 6 hydroxyl groups in a molecule, a plurality of isomers are produced depending on the position of the dehydrated hydroxyl group. 2,5-sorbitan is produced by selecting a reaction condition, and isomannide can be produced through an intermediate 1,4-mannitan by adjusting the reaction condition to a different condition. There are many different kinds of side reactions as described above, and therefore, in order to increase the yield of a specific target substance, development of a catalyst having high selectivity and development of a chemical reaction control technique using said catalyst are required.

For example, Patent Literature 1 discloses a method for obtaining isomannide by dehydrating mannitol in the presence of an acid catalyst that is a homogeneous catalyst, such as sulfuric acid or hydrogen chloride, as a conventional method. If such a homogeneous catalyst is used, a step of removing the acid from a reaction product becomes complicated, the cost of handling equipment for using a liquid or gaseous strong acid increases, and the burden of safety also becomes a big problem.

Patent Literature 2, Example 45 discloses a method for obtaining isomannide from mannitol using, as a catalyst, water-resistant Lewis acid such as bismuth(III) triflate and, according to this, isomannide is obtained in a yield of 61% at a temperature of about 160° C. and under a pressure of 20 torr. However, there are environmental and safety problems because a heavy metal such as a bismuth compound is used. Moreover, even if the catalyst is solid in an unused state, it is dissolved in mannitol during the reaction, and therefore, it is difficult to separate and remove the catalyst from the final product. On that account, a solid catalyst that is easy to recover and that can be reused is strongly desired.

Non-Patent literature 1 describes that mannitol can be converted into 2,5-sorbitan and isomannide by hydrothermal reaction in water at 250° C. for 30 hours under noncatalytic conditions. Although this method is preferable from the viewpoint that a catalyst such as toxic gas is not used, it requires a high temperature and long-term reaction, and not only is the production efficiency low but the energy efficiency is also low, so that it is hard to say that this method is practical.

If dehydration reaction of mannitol is to be carried out in water, the equilibrium shifts to the reverse reaction because of the water, and therefore, the yield is generally lowered. Even if use of an organic solvent other than water is attempted to improve it, a high temperature and a high pressure are required, the cost of the reactor increases, and in addition, such a method is undesirable also from the viewpoints of environmental preservation and safety.

The method for producing the corresponding anhydrosugar from mannitol, described in the Patent or Non Patent Literature mentioned above, is assumed to synthesize a single target substance (e.g. isomannide) from a starting material. However, these production facilities are expensive, and mass production requires a large amount of facility investment. If different useful substances can be synthesized from the same starting material under similar reaction conditions by simply changing a catalyst, the initial investment for the production facilities to produce them can be reduced, so that such synthesis is preferable.

As described above, sulfuric acid, toxic gas catalysts such as hydrogen chloride, and heavy metal complex catalysts such as bismuth are conventionally known as catalysts for the dehydration reaction of mannitol. In actuality, any catalyst having overcome the defects of the conventional catalysts, that is, any catalyst which can be easily separated and removed from a product, is excellent in handling safety and recycling properties, can carry out a reaction at a mild temperature and atmospheric or close to atmospheric pressure, and provides a high reaction yield for a short period of time, has not been realized yet, and achieving such a catalyst has been desired.

CITATION LIST

Patent Literature

Patent Literature 1
Laid-Open Japanese Patent No S57-165386-A
Patent Literature 2
Laid-Open Japanese Patent No 2016-516014-A

Non Patent Literature

Non Patent Literature 1
M. Shiral et al. RSC Adv., 4, 45575 (2014)

SUMMARY OF INVENTION

Technical Problem

It is an object of the present invention to provide a solid acid catalyst which can be used to obtain isomannide and/or 2,5-sorbitan from mannitol, e.g. mannitol derived from cellulose and/or hemicellulose that is a main component of biomass, in a high yield at a low cost with high selectivity and high safety, and a process for producing isomannide and/or 2,5-sorbitan using this solid acid catalyst.

It is another object of the present invention to provide a catalyst for producing isomannide and/or 2,5-sorbitan from mannitol, the catalyst having an excellent performance after repeated regeneration thereof.

It is a further object of the present invention to provide a process for producing isomannide and/or 2,5-sorbitan from mannitol under mild conditions without requiring introduction of water or an organic solvent into the reaction system.

It is a still further object of the present invention to provide a process for selectively producing isomannide and 2,5-sorbitan in desired amounts with the use of the same reactor and the same starting material (mannitol) simply by changing the catalyst used and/or the reaction conditions.

The objects of the present invention will be apparent also from the following description.

Solution to Problem

In light of the above circumstances, the present inventors have conducted extensive research in order to overcome the defects of the prior art, and as a result, acquired the guidelines described below as thoughts on how to achieve the objects of the present invention.
(1) First, using sulfuric acid that is a typical example of a conventional acid catalyst, a reaction was carried out at a relatively low temperature without using a water solvent, and as a result, the conversion of mannitol reached near 100%, while the yield of isomannide that was a desired substance was about 20%, and the yield of sorbitan that was a desired substance was 26%. By-products other than the desired substances made up about 50%, and it was found that the by-products lowered the production yield. From this, it can be seen that a catalyst that not only has enhanced acidity of an acid but also stereoselectively accelerates a reaction is required as the dehydration catalyst.
(2) No example of a heterogeneous catalyst having a high acid strength and capable of stereoselectively accelerating a reaction as described above was known, and therefore, studies were conducted first with a focus on zeolites and other solid acids, as acid catalysts that are relatively easily obtainable, are of low cost and have high safety.
(3) At first, selection of a catalyst and research into a catalytic amount by which isomannide or 2,5-sorbitan could be selectively obtained in the complicated reaction steps were carried out so that the reaction time could be shortened and the yield could be increased.
(4) The present inventors then thought that the reactivity depended on acid strength, and they tested H-mordenite having a high acid strength and acidic ion-exchange resins, using sulfuric acid as a comparative example, but this did not result in any materials showing satisfactorily high reaction activity.
(5) The present inventors further investigated zeolites containing silica having higher activity, with a focus on zeolite catalysts having high acidity, and were surprised to find that there was a strong correlation between the yield of 2,5-sorbitan (monoanhydrosugar) and isomannide (dianhydrosugar) that are dehydration products of mannitol and pore structures of zeolite catalysts.
(6) Specifically, it was found that, of the zeolites called solid superacids, β-type zeolite was particularly preferable for obtaining isomannide with high selectivity.
(7) Further, the properties were examined by changing the atomic composition ratio of Si to Al (Si/Al ratio), said Si and Al being zeolite components, and as a result, it was found that, when the Si/Al ratio was 10 to 300, a good isomannide yield was exhibited and, particularly when the Si/Al ratio was in the range of 25 to 150, the yield of isomannide became the highest.
(8) In general, as the Si/Al decreases, the acidity increases, and as the Si/Al increases, the acid strength increases. It was assumed that the result of (7) above indicated that, because both the acidity and the acid strength acted on the dehydration of mannitol and the conversion into isomannide, the aforementioned range was the optimum one.
(9) Based on the above assumption, a reaction to obtain 2,5-sorbitan using mannitol as a starting material was also carried out by changing the zeolite structure similarly to the above, and as a result, Y-type zeolite (especially H-Y-type zeolite) was found to be particularly preferable and, when the Si/Al ratio was around 40, a high yield of 2,5-sorbitan was obtained.
(10) As described above, it was found that when a reaction to selectively obtain 2,5-sorbitan or isomannide from mannitol was carried out, the pore structure of zeolites used had strong influence, and moreover, both the acid strength and the acidity acted on the reactivity. As a result, the present invention has been accomplished.

That is to say, the present invention relates to the following.
1. A solid, dehydration catalyst comprising an H-type β zeolite and/or a Y-type zeolite, for producing 2,5-sorbitan and/or isomannide from mannitol.
2. The solid catalyst according to 1 above for preferentially producing isomannide, exclusively comprising an H-type β zeolite.
3. The solid catalyst according to 1 above for preferentially producing 2,5-sorbitan, exclusively comprising a Y-type zeolite.
4. The solid catalyst according to any one of 1 to 3 above, wherein the zeolite has a Si/Al ratio (atomic composition ratio) of 10 to 300.
5. The solid catalyst according to 4 above, wherein the Si/Al ratio (atomic composition ratio) of the zeolite is 25 to 150.
6. The solid catalyst according to 5 above, wherein the Si/Al ratio (atomic composition ratio) of the zeolite is 40 to 100.
7. The solid catalyst according to any one of 1 to 6 above, having a specific surface area, as determined by BET method, of 200 to 600 m$^2$/g.
8. The solid catalyst according to any one of 1 to 7 above, having a three-dimensional pore structure with a pore volume of 0.4 to 0.8 cm$^3$/g and a pore diameter of 6 to 8 Angstroms, as determined by BET method.
9. The solid catalyst according to any one of 1 to 8 above, having an acidity of 0.028 mmol/g to 0.67 mmol/g, as determined by a method of NH$_3$-TPD.
10. A process for producing 2,5-sorbitan and/or isomannide from mannitol, comprising the steps of:
(a) adding the catalyst according to any one of 1 to 9 above to mannitol to obtain a reaction mixture, and
(b) heating the reaction mixture obtained in step (a) to a temperature of 110° C. to 170° C. at ambient pressure or under reduced pressure.
11. The process according to 10 above, wherein the amount of the catalyst is 5 to 50% by weight, based on the 100% by weight of the mannitol.
12. The process according to 10 or 11 above, wherein the catalyst exclusively comprises an H-type β zeolite, and isomannide is preferentially produced.
13. The process according to any one of 10 to 12 above, wherein isomannide is produced through 1,4-mannitan.

14. The process according to 10 or 11 above, wherein the catalyst exclusively comprises a Y-type zeolite, and 2,5-sorbitan is preferentially produced.

15. A process for selectively producing isomannide from mannitol or 2,5-sorbitan from mannitol with the use of the same manufacturing apparatus by selecting any of an H-type β zeolite, a Y-type zeolite or a mixture thereof as the catalyst to dehydrate the mannitol.

16. Use of an H-type β zeolite and/or a Y-type zeolite as a solid dehydration catalyst for producing 2,5-sorbitan and/or isomannide from mannitol.

17. Use of an H-type β zeolite as a solid dehydration catalyst for preferentially producing isomannide from mannitol.

18. Use of a Y-type zeolite as a solid dehydration catalyst for preferentially producing 2,5-sorbitan from mannitol.

DESCRIPTION OF EMBODIMENTS

Figure 1:
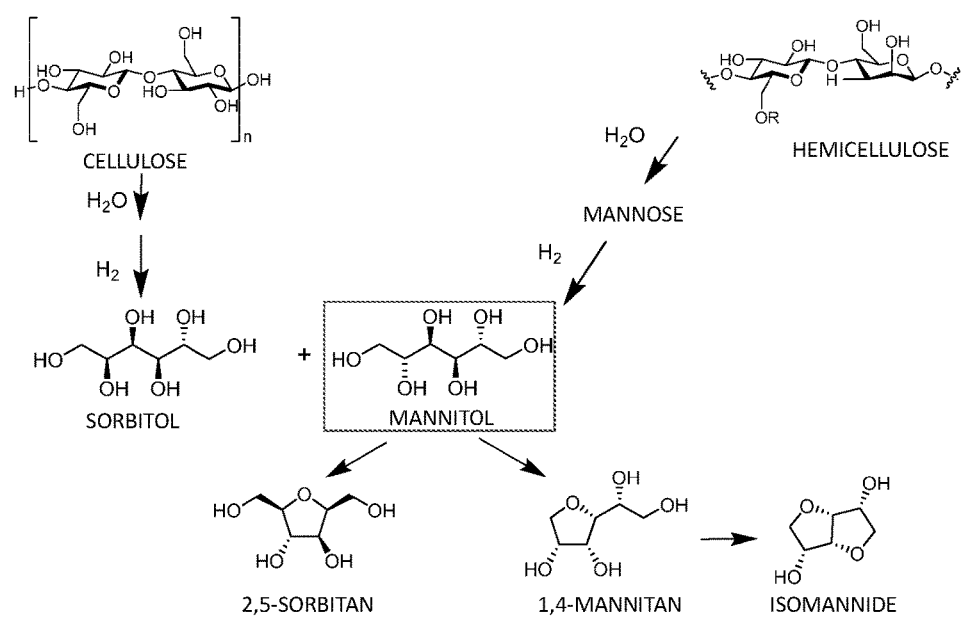
FIG. 1 shows a reaction scheme relating to conversion of mannitol into 2,5-sorbitan and conversion of mannitol into isomannide through 1,4-mannitan.

Each step of conversion of mannitol into 1,4-mannitan or 2,5-sorbitan and conversion of 1,4-mannitan into isomannide proceeds while an equivalent amount of water is produced. The reaction scheme is shown in FIG. 1. The present invention provides an improved process for producing 2,5-sorbitan that is a monoanhydride of mannitol from mannitol and for producing isomannide from mannitol through a dehydrated intermediate 1,4-mannitan. Although the origin of mannitol used in the present invention is not specifically limited, mannitol used in the present invention can be obtained from, for example, various plant raw materials. In a preferred embodiment of the present invention, mannitol obtained by a dehydration reaction and hydrogenation of cellulose and/or hemicellulose that are starting materials obtained from biomass is used (FIG. 1). In nature, d-mannitol exists in a large amount, but any of d-mannitol and 1-mannitol (and a mixture thereof) can be used as the mannitol.

An acid catalyst is preferably used as the catalyst in the present invention. In order to achieve the objects of the present invention, it is preferable to use a catalyst enabling efficient one-stage or two-stage dehydration of mannitol and having a function to highly selectively obtain a desired substance from mannitol. In the present invention, H-type β zeolite and/or Y-type zeolite is used as such a catalyst.

Although it has also been found in the present invention that the conversion of mannitol and the selectivity into the final product vary depending on the pore structure of the zeolites used, and it is more preferable that, in order to efficiently obtain isomannide from mannitol, β-type zeolite be used, in order to obtain 2,5-sorbitan as a target substance, it is more preferable that Y-type zeolite be used.

Accordingly, the solid catalyst for dehydration reaction in the present invention is a catalyst comprising an H-type β zeolite and/or a Y-type zeolite. In an embodiment of the present invention, said catalyst substantially comprises, as the catalytically active components, H-type β zeolite(s) and/or Y-type zeolite(s) only.

The catalyst can comprise, for example, a binder and/or silica in such a range as not to impair the effect of the present invention, in addition to the H-type β zeolite and/or the Y-type zeolite.

The catalyst may be free of components other than H-type β zeolites and/or Y-type zeolites, that is to say, the catalyst can substantially consist of only H-type zeolite(s) and/or Y-type zeolite(s). In this case, the present invention relates to a solid dehydration catalyst for producing 2,5-sorbitan and/or isomannide from mannitol, wherein said solid dehydration catalyst is H-type β zeolite(s) and/or Y-type zeolite(s).

In an embodiment of the present invention, a mixture comprising 2,5-sorbitan and isomannide is obtained by dehydrating mannitol using the catalyst.

In this embodiment, if the catalyst exclusively comprises an H-type β zeolite, isomannide is produced preferentially to any other components (e.g. 2,5-sorbitan); that is, it is produced in a higher yield than the yield of any other component. For example, isomannide is produced in a yield ((weight of isomannide produced/weight of starting material)×100) of 25% to 100%, for example, 30 to 70%, and is produced preferably in a yield of no less than 40%, and more preferably no less than 50%, for example, more than 50%. In this case, other components (e.g. 2,5-sorbitan) each exhibit a yield of less than 50%, no more than 40%, no more than 30% or no more than 25%. The yields of other components are each lower than the yield of isomannide, and preferably, the total yield of other components is lower than the yield of isomannide. Here, the expression "exclusively comprises an H-type β zeolite" means that the catalyst substantially comprises an H-type β zeolite only, as the catalytically active component.

In the above embodiment, if the catalyst exclusively comprises a Y-type zeolite, 2,5-sorbitan is produced preferentially to any other components (e.g., isomannide); that is, is produced in a higher yield than the yield of any other component. For example, 2,5-sorbitan is produced in a yield ((weight of 2,5-sorbitan produced/weight of starting material)×100) of 30% to 100%, for example, 30 to 70%, and is produced preferably in a yield of no less than 40%, and more preferably no less than 50%, for example, more than 50%. In this case, other components (e.g. isomannide) each exhibit a yield of less than 50%, no more than 40%, no more than 30% or no more than 25%. The yields of other components are each lower than the yield of 2,5-sorbitan, and preferably, the total yield of other components is lower than the yield of 2,5-sorbitan. Here, the expression "exclusively comprises a Y-type zeolite" means that the catalyst substantially comprises a Y-type zeolite only, as the catalytically active component.

The catalyst can comprise both of H-type β zeolite(s) and Y-type zeolite(s). By mixing both in an appropriate mixing ratio and using the resulting mixture, it is possible to obtain isomannide and 2,5-sorbitan in a desired ratio.

Here, a zeolite is a generic term for crystalline porous aluminosilicates, and of zeolites, an H-type β zeolite and/or a Y-type zeolite is used in the present invention, as described above.

A β-Zeolite is a zeolite in which the unit cell composition is represented by the following average composition formula.

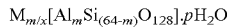

$$M_{m/x}[Al_mSi_{(64-m)}O_{128}] \cdot pH_2O$$

wherein M is a cation species (e.g. Na$^+$), x is a valence of M, m is a number larger than 0 but smaller than 64, and p is the number 0 or larger.

An acid type β zeolite is also called H-type β zeolite or proton-type β zeolite, and has a structure in which the cation sites of the β zeolite have been ion-exchanged and thereby replaced with H$^+$. When the H-type β zeolite is used in the present invention, a slight amount of the M that has not been replaced may be contained in the H-type β zeolite in such a range as not to impair the effect of the present invention. The H-type β zeolite is widely used for catalysts for various reactions, adsorbents for chemical substances, etc. because the H$^+$ acts as a Broensted acid.

The production process for the H-type β zeolite is already known, and various products are commercially available. Some examples of the H-type β zeolite employable in the present invention are H-BEA-25 (Si/Al=12.5) manufactured by Clariant Catalysts (Japan) K.K., CP814C (Si/Al=19) manufactured by Zeolyst International, H-BEA-50 (Si/Al=25) manufactured by Clariant Catalysts (Japan) K.K., HSZ-960-HOA (Si/Al=50) manufactured by Tosoh Corporation, H-BEA-150 (Si/Al=75) manufactured by Clariant Catalysts (Japan) K.K., CP811C-300 (Si/Al=150) manufactured by Zeolyst International, HSZ-980-HOA (Si/Al=250) manufactured by Tosoh Corporation, or the like, which are commercially available.

The surface hydrophilicity, acidity and acid strength of a zeolite greatly vary depending upon the ratio between Si and Al that constitute zeolite crystals. In general, as the Si/Al ratio (atomic ratio) increases, the hydrophilicity decreases, the acidity decreases, and the acid strength increases.

In an embodiment of the present invention, the Si/Al ratio of the H-type zeolite can be 10 to 300, and in this range, not only is a better conversion of mannitol obtained but also better reaction selectivity can be attained. The Si/Al ratio is more preferably in the range of 15 to 280, for example, 20 to 250 or 20 to 200, even more preferably in the range of 25 to 150, and particularly preferably in the range of 40 to 100, for example, 45 to 80 or 50 to 75. As described above, H-type β zeolites with various Si/Al ratios can be commercially available.

A Y-type zeolite is one of faujasite-type zeolites, and is a zeolite having a structure in which counter cations have been inserted in a lattice structure formed of aluminosilicate having negative charges.

In the present invention, for example, a zeolite having the following composition can be used as the Y-type zeolite.

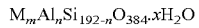

$$M_mAl_nSi_{192-n}O_{384} \cdot xH_2O$$

wherein M represents a counter cation, m and x each represent a positive real number, and n represents a real number in the range of 48 to 76.

In the above composition formula, m is determined depending on n and the valence of M, and for example, when M is a monovalent cation, m is equal to n. For example, when the M is H, this zeolite is also called HY-type zeolite, and when the M is Na, this zeolite is also called NaY-type zeolite.

It is known that the Y-type zeolite is enhanced in thermal stability by removing Al from the skeletal structure of the zeolite through acid treatment or steaming treatment, and the zeolite thus obtained is called ultra-stable Y (USY) type zeolite. The term "Y-type zeolite" as used herein also includes such USY-type zeolite.

Examples of the Y-type zeolites that can be used in the present invention include various known Y-type zeolites such as NaHY-type zeolite, NaNH$_4$Y-type zeolite, NH$_4$Y-type zeolite and DASY-type zeolite, in addition to those previously mentioned.

In a preferred embodiment of the present invention, the Y-type zeolite is HY-type zeolite or USY-type zeolite (e.g. H-USY-type zeolite).

The production process for the Y-type zeolite is already known, and various products are commercially available. As the Y-type zeolite that can be used in the present invention, for example, H-USY manufactured by Zeolyst International, Si/Al=40, CBV780 is commercially available.

In an embodiment of the present invention, the Si/Al ratio of the Y-type zeolite can be 10 to 300, and in this range, not only is a better conversion of mannitol obtained but also better reaction selectivity can be attained. The Si/Al ratio is more preferably in the range of 15 to 280, for example, 20 to 250 or 20 to 200, even more preferably in the range of 25 to 150, and particularly preferably in the range of 30 to 100, for example, 35 to 80 or 35 to 45. Y-Type zeolites with various Si/Al ratios are commercially available.

The atomic composition ratio (atomic ratio) of Si to Al (Si/Al ratio) can be measured by elemental analysis using high-frequency inductively coupled plasma optical emission spectrometry (ICP emission spectrometry). First, a fixed amount of a zeolite and borax are melted and dissolved in an acid. The resulting solution is diluted to an assumed concentration (20 ppm), followed by measurement by ICP. Quantitative calculation is carried out by comparing the measurement result with a calibration curve based on the ICP results of a standard solution containing the elements.

In an embodiment of the present invention, a zeolite for use in the present invention can have a specific surface area of 50 m$^2$/g to 1000 m$^2$/g. From the viewpoint that although the adsorption performance of the zeolite is sufficiently ensured, the proper desorption of the product is not inhibited, the zeolite in the present invention preferably has a specific surface area of 100 m$^2$/g to 800 m$^2$/g, and particularly preferably 400 m$^2$/g to 700 m$^2$/g, for example, 200 to 600 m$^2$/g.

The specific surface area can be measured by BET method in accordance with JIS 8830 (based on adsorption of nitrogen gas at a liquid nitrogen temperature). In the measurement, a commercially available specific surface area measuring device (e.g. model: Macsorb Model-1210 manufactured by Mountech Co., Ltd.) can be used. In pretreatment, a sample is maintained at 400° C. for 2 hours, and the sample after the pretreatment is subjected to measurement under the following measurement conditions, whereby a BET specific surface area can be determined.

Treatment gas: a mixed gas containing 30% by volume of nitrogen and 70% by volume of helium (corresponding to relative pressure P/P$_0$=0.1 to 0.3)

Measuring method: single-point method

In an embodiment of the present invention, a zeolite for use in the present invention can have a pore volume of 0.2 to 1.0 cm$^3$/g. From the viewpoint that although sufficient adsorption-desorption of mannitol and a dehydration product thereof is made possible in order to realize expected reaction efficiency, but on the other hand, the catalyst's shape is maintained, the zeolite for use in the present invention more preferably has a pore volume of 0.4 to 0.8 cm³/g. Such a pore volume is preferable because conversion and selectivity are enhanced. The pore volume can be measured by BET method; that is, of the data obtained based on the BET specific surface area at relative pressures in the range of not less than 0.95 but less than 1, the gas adsorption quantity closest to that at a relative pressure of 1 is converted into a liquid, whereby a pore volume can be determined.

In an embodiment of the present invention, the zeolite for use in the present invention has a three-dimensional pore structure having a pore diameter of 4 to 10 Angstroms. From the viewpoint that although mannitol molecules easily enter, selective adsorption is not inhibited so as to not lower the selectivity of the reaction, the zeolite for use in the present invention preferably has a three-dimensional pore structure with a pore diameter of 6 to 8 Angstroms. As the pore diameter, a measured value determined from a $N_2$ adsorption isotherm can be used.

In an embodiment of the present invention, the acidity in the zeolite catalyst for use in the present invention can be 0.010 mmol/g to 1.0 mmol/g. From the viewpoint that although such sufficient activity that does not lower the conversion of mannitol is obtained, selectivity into a desired substance is not lowered either, the zeolite catalyst for use in the present invention preferably exhibits an acidity of 0.028 mmol/g to 0.67 mmol/g. The acidity in the catalyst can be determined by $NH_3$-TPD method. The $NH_3$-TPD method refers to a temperature-programmed desorption method using an ammonia component as an adsorbed molecule, and refers to a non-equilibrium technique in which with continuously raising the temperature of a catalyst sample, the process of desorption of an adsorbed ammonia molecule is measured to thereby evaluate an acidity on the catalyst.

In order to produce 2,5-sorbitan and/or isomannide from mannitol using the solid catalyst of the present invention, for example, a zeolite catalyst is added to mannitol and, after mixing both or while mixing both, they are heated, whereby a dehydration reaction can be carried out. A desired target product (2,5-sorbitan and/or isomannide) can be obtained by the dehydration reaction.

The above mixing can be carried out by, for example, stirring, and the stirring can be carried out by using e.g. a stirrer or a stirring blade. For example, when the amounts of mannitol and catalyst are small, both are stirred and mixed using a stirrer, and when the amounts thereof are large, stirring can be carried out e.g. by means of ribbon type stirring blades based on motor drive.

In a preferred embodiment of the present invention, mixing of mannitol and the catalyst is carried out using a stirrer or a stirring blade because homogeneous and sufficient mixing can be achieved.

In such dehydration reaction of mannitol, if the amount of the zeolite comprised in the catalyst or, when the catalyst substantially consists only of a zeolite, the amount of the zeolite as the catalyst (both amounts also being simply referred to as "catalytic amount" hereinafter) is too small, a sufficient reaction rate is not obtained, and the conversion of mannitol is lowered; on the other hand, if the catalytic amount is too large, not only is the catalyst wasted but also the side reaction is accelerated and the yield of 2,5-sorbitan and/or isomannide may be conversely decreased. From such viewpoints, the amount of the catalyst according to the present invention is preferably 1 to 60% by weight, more preferably 2 to 50% by weight, for example, 5 to 40% by weight, and particularly preferably 10 to 30% by weight, for example, 20 to 30% by weight or 25 to 30% by weight, relative to 100% by weight of mannitol.

The reaction system is constituted of mannitol and zeolite catalyst as the main components. If water is added, the reaction mixture is decreased in viscosity and is easily mixed at a low temperature, but the reaction yield is liable to decrease because the equilibrium shifts in the opposite direction (to starting material side). Although it is possible to increase the dehydration rate by increasing the degree of vacuum in the reactor, the production cost therefor is liable to increase. In the present invention, therefore, the above reaction is preferably carried out without adding water, even though the reaction can be carried out regardless of the presence or absence of water.

The reaction can be carried out while mixing and stirring mannitol and the zeolite in the absence of a solvent and, if necessary, while deaerating the reaction chamber. It is also possible to appropriately add organic acids such as acetic acid or inorganic acids other than zeolites, when needed, but a by-product is liable to occur, and separation and removal of the catalyst after the reaction tends to become complicated. In a preferred embodiment of the present invention, therefore, the above reaction is carried out without adding a solvent.

Even if the reaction is carried out without adding water or a solvent, the dehydration reaction begins when a mixture of mannitol and zeolite catalyst is heated, and water and isomannide are produced, so that these can also function as solvents.

The dehydration reaction in the present invention can be carried out by maintaining a mixture of catalyst and mannitol at an arbitrary pressure. The dehydration reaction is preferably carried out at ambient pressure or under reduced pressure.

It is possible to carry out the reaction at normal pressure (at ambient pressure) without reducing pressure in the reactor. However, because of the water generated by the dehydration, the water vapor pressure increases in the reactor, and the chemical equilibrium shifts to the starting material side and the reaction rate is liable to decrease. In order to prevent this, it is also preferable to slightly depressurize and deaerate the reactor. When the reaction is carried out under reduced pressure, the reaction is conducted at a pressure of, for example, no more than 1000 hPa, no more than 850 hPa, no more than 750 hPa, no more than 500 hPa, no more than 400 hPa or no more than 10 hPa. On the other hand, the lower limit of the pressure depends only upon the reactor used and is not specifically limited, but in general, it is enough just to conduct the reaction at a pressure of 5 hPa to ambient pressure.

In the reaction of the present invention, control of the reaction temperature is extremely important.

The reaction temperature for the dehydration reaction is generally between 100° C. and 200° C., preferably between 110° C. and 170° C., and more preferably between 120° C. and 160° C., for example, 130° C. to 160° C. or 135° C. to 155° C. If the temperature is lower than these ranges, the reaction rate may decrease, and if the temperature is too high, the reaction selectivity into the desired 2,5-sorbitan and/or isomannide decreases, and a by-product is liable to occur, or coking on the catalyst tends to occur, and as a result, the reaction rate may decrease.

In an embodiment of the present invention, dehydration reaction of mannitol is carried out by adding the catalyst to mannitol, and heating the mixture to a temperature in one of the above ranges, followed by maintaining this temperature; that is, maintaining the temperature at the same temperature as the heating temperature, or maintaining the temperature at a temperature that is in one of the above ranges but differs from the initial heating temperature, and as a result, desired products (2,5-sorbitan and/or isomannide) can be obtained.

Mannitol as a starting material is solid at room temperature. The reaction may be carried out by mixing the solid mannitol as it is with the catalyst, or the dehydration reaction may be carried out while melting the mannitol by heating the mannitol to not lower than the melting point thereof, or after melting the mannitol.

When a mixture of mannitol and catalyst is heated at the aforementioned reaction temperature, dehydration reaction begins even at a temperature no higher than the melting point of mannitol, and the water and isomannide (melting point: 82° C.) generated also function as solvents. Therefore, even when the reaction is carried out after (or while) mixing solid mannitol as it is with the catalyst, the system is dissolved after the dehydration reaction begins in the solid state, and consequently, the dehydration reaction favorably proceeds even when the reaction temperature is not higher than the melting point of mannitol.

If the reaction time of the dehydration reaction in the present invention is too short, a sufficient yield of 2,5-sorbitan and/or isomannide cannot be achieved, and therefore, the reaction time is preferably no less than 15 minutes, and more preferably no less than 30 minutes. However, if it is too long, the cost as well as the occurrence of by-products increase and become concerns. From such a viewpoint, the reaction time is preferably 30 minutes to 10 hours, and more preferably 1 to 5 hours, for example, 1 to 4 hours.

In the process of the present invention, for example, a zeolite that is a solid acid catalyst can be mixed as it is with mannitol that is a starting material, and the reaction can be carried out at such a predetermined temperature for such a predetermined time as above, that is, the reaction can be carried out batch-wise. Alternatively, the reaction can be continuously carried out by filling a reaction tube with a shaped zeolite catalyst and introducing molten mannitol thereinto to allow it to pass through.

In an embodiment of the present invention, mannitol is heated to no lower than the melting point thereof to start the reaction. Next, while removing water generated in the reaction system by evaporation, the temperature is raised over time, thereby increasing the yield. The reaction is usually carried out at a temperature between 100° C. and 200° C., and preferably between 110° C. and 170° C., but it is also possible to carry it out at a temperature outside of these ranges. The reaction can be carried out at an almost constant reaction temperature, but the temperature can be also graded over time from the aforesaid low temperature to higher temperature. If a final product (2,5-sorbitan) is obtained from a sugar alcohol (mannitol) by one-stage dehydration, or if, in the case of two-stage reaction, the first stage (condensation to form an intermediate) is a rate-determining step, the reaction can be carried out in a reaction temperature region of almost constant temperature. On the other hand, if the stage of condensation of an intermediate (monoanhydrosugar: 1,4-mannitan) to form a final product (dianhydrosugar: isomannide) is a rate-determining step in a two-stage dehydration process, it is also preferable that the second stage be performed in a temperature range higher than that in the first stage, preferably for said second stage, because the yield is enhanced in a short period of time.

In an embodiment of the present invention, the present invention relates to a process for producing 2,5-sorbitan and/or isomannide from mannitol, comprising the steps of:
(a) adding the catalyst to mannitol to obtain a reaction mixture, and
(b) heating the reaction mixture obtained in step (a) to a temperature of 110° C. to 170° C. at ambient pressure or under reduced pressure.

In an embodiment of the present invention, the above process can further comprise the step of:
(c) maintaining the reaction temperature at the same temperature as the temperature in step (b), preferably for 15 minutes or longer.

As previously described, when the catalyst exclusively comprises H-type zeolite, isomannide can be produced preferentially to any other component. When the catalyst exclusively comprises Y-type zeolite, 2,5-sorbitan can be produced preferentially to any other component.

In a preferred embodiment of the present invention, isomannide is produced through an intermediate 1,4-mannitan.

As the reactor for the dehydration reaction, for example, a reactor including a reaction vessel with a heating device, a stirring device, inlets for a catalyst and a starting material (mannitol), an exhaust vent connected to a vacuum device for reducing pressure and an outlet for a product, and capable of carrying out the reaction while measuring the temperature by a thermometer and monitoring the degree of vacuum by a manometer can be used. The pressure in the reactor may be atmospheric, or the reactor may be slightly deaerated as previously described, and the pressure is not specifically limited as long as it is not higher than atmospheric pressure.

After the reaction is completed, the zeolite catalyst is removed from the reaction system by, for example, filtering the catalyst, whereby the desired reaction product can be isolated. The catalyst can easily be separated and removed, complicated neutralization and removal of an acid becoming unnecessary, thereby presenting a remarkable advantage in terms of productivity. The zeolite catalyst once used can be reused if subjected to washing and drying after separation, meaning that there are environmental preservation and cost-reduction merits.

In a further embodiment of the present invention, the present invention relates to the use of an H-type β zeolite and/or a Y-type zeolite as a solid dehydration catalyst for producing 2,5-sorbitan and/or isomannide from mannitol.

In a still further embodiment of the present invention, the present invention relates to use of an H-type β zeolite as a solid hydration catalyst for preferentially producing isomannide from mannitol. In a still further embodiment of the present invention, the present invention relates to the use of a Y-type zeolite as a solid dehydration catalyst for preferentially producing 2,5-sorbitan from mannitol.

By using the catalyst of the present invention, particularly preferably by using an H-type β zeolite, isomannide can be preferably obtained from mannitol by means of two-stage dehydration via 1,4-mannitan. If necessary, by changing the catalyst to, for example, a Y-type zeolite, 2,5-sorbitan can also be preferably produced from the same mannitol, with the use of the same reactor. By mixing the H-type β zeolite and the Y-type zeolite in appropriate amounts, it is also possible to obtain isomannide and 2,5-sorbitan in a desired composition ratio. It is preferable that the product be able to be controlled simply by selecting and adjusting the type of the catalyst and the reaction conditions as described above, because the production apparatus can be effectively utilized in conformity to the needs of the market.

The 2,5-sorbitan that is monoanhydrosugar obtained by using the catalyst of the present invention can be widely used as a plant-derived surfactant in emulsifying agent applications for e.g. cosmetics and food. The isomannide that is dianhydrosugar is useful as a material for plastics such as polyester, polycarbonate and polyurethane, and besides, the isomannide is expected to have a wide range of applications also as a material for pharmaceuticals, etc.

The present invention will be described below with reference to the examples. Examples 1 to 4 were carried out by changing the type of zeolite catalyst and the reaction temperature, and changes of products with time are shown as graphs (FIGS. 2 to 5). Table 1 shows results of analyses of products obtained when the reaction was carried out at a fixed temperature (150° C.) for one hour (Examples 5 to 12 and Comparative Examples 1 to 5). The present invention is not limited in any way by these examples.

EXAMPLES

Example 1

Figure 2:
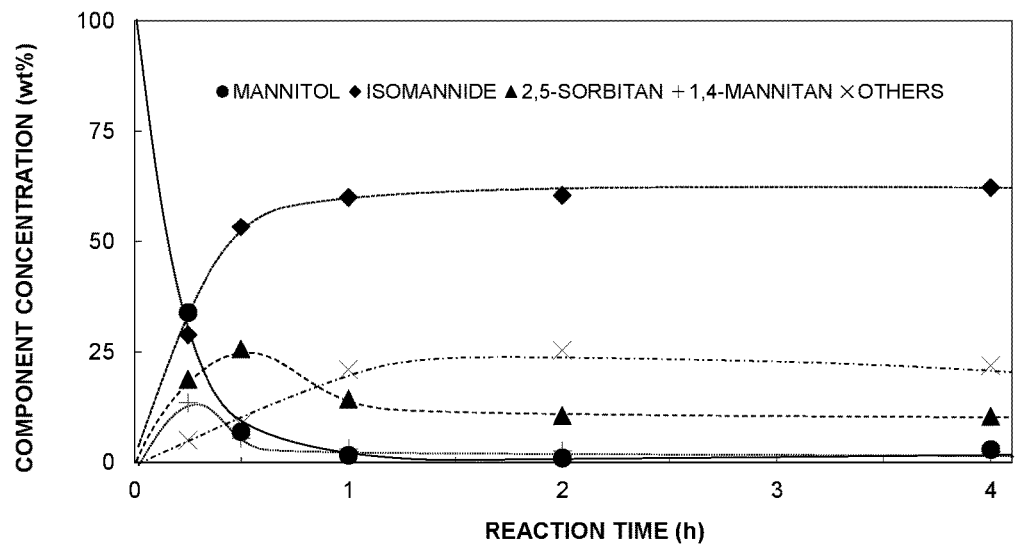
FIG. 2 shows results of analyses of mannitol, 2,5-sorbitan, 1,4-mannitan and isomannide, the results being obtained when a dehydration reaction (150° C.) of mannitol was carried out using H-type β zeolite (Si/Al=75) (Example 1).

The reaction was carried out by mixing mannitol and an H-type β zeolite (Si/Al=75, Clariant Catalysts (Japan) K.K., H-BEA-150) in a glass container under a pressure of 400 hPas. The weight of the β zeolite was 28% of the weight of mannitol. The container was heated to 150° C. and, while maintaining the container at the same temperature for 4 hours, the dehydration reaction was carried out. Samples were taken from the reaction mixture at predetermined intervals, and the mannitol, 2,5-sorbitan, 1,4-mannitan and isomannide were analyzed. The results are shown in FIG. 2. The mannitol concentration steadily decreased as a function of time and, after about 60 minutes, it reached almost 0. At the same time, the isomannide concentration steadily increased and, after about 60 minutes, it stabilized at almost 61%. In the initial reaction stage, mannitol was condensed into 2,5-sorbitan and the maximum yield of the latter of 26% was observed, but when the reaction was continued further, the yield decreased. The 1,4-mannitan concentration exhibited a peak value early, and after one hour, it became almost 0.

Example 2

Figure 3:
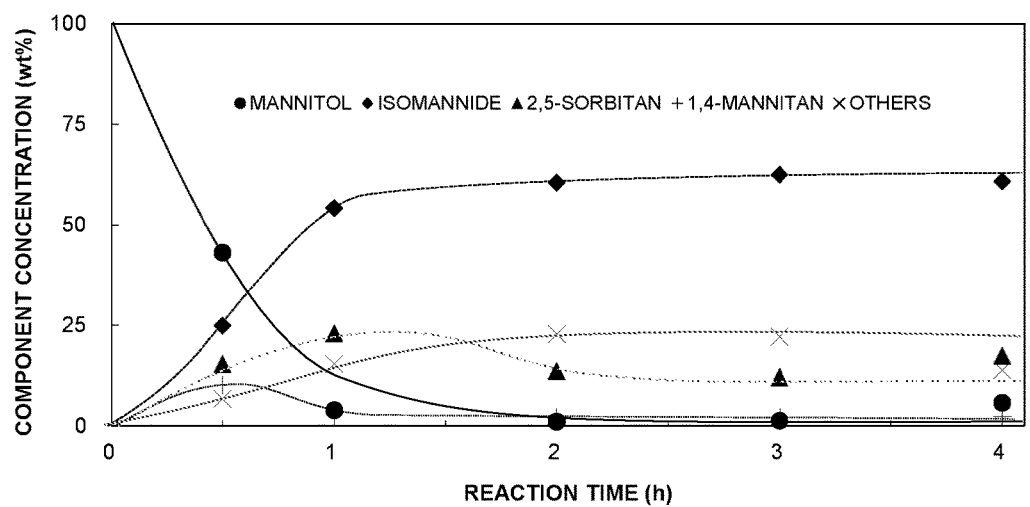
FIG. 3 shows results of analyses of mannitol, 2,5-sorbitan, 1,4-mannitan and isomannide, the results being obtained when a dehydration reaction (140° C.) of mannitol was carried out using H-type β zeolite (Si/Al=75) (Example 2).

Reaction was carried out in the same manner as in Example 1, except that the reaction temperature was changed to 140° C. The results are shown in FIG. 3. The mannitol concentration steadily decreased as a function of time, and after about 60 minutes, it became almost 0. At the same time, the isomannide concentration steadily increased and, after about 60 minutes, it reached almost 63% and stabilized. First, 2,5-sorbitan was condensed from mannitol, and was produced in a maximum yield of 23%, but the yield subsequently decreased. The 1,4-mannitan concentration increased a little at first, but after one hour, it reached almost 0.

Example 3

Figure 4:
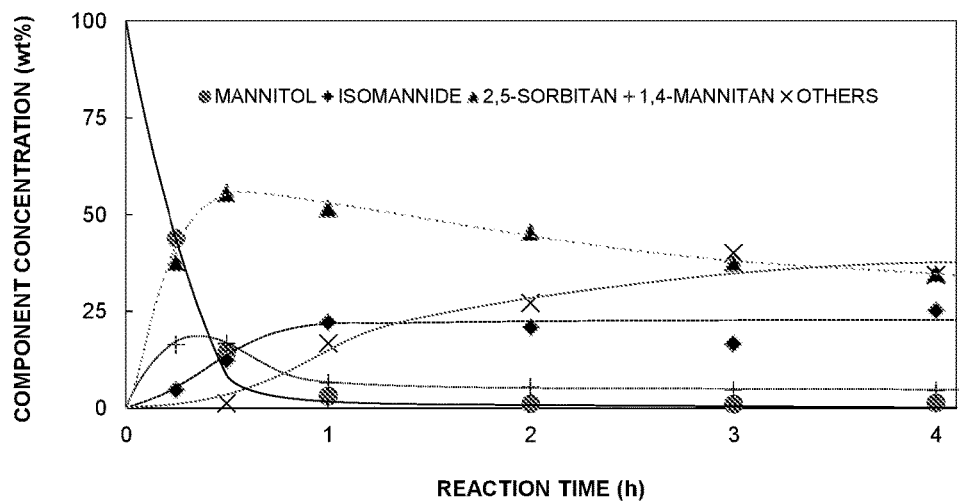
FIG. 4 shows results of analyses of mannitol, 2,5-sorbitan, 1,4-mannitan and isomannide, the results being obtained when a dehydration reaction (150° C.) of mannitol was carried out using H-type H-USY zeolite (Si/Al=40) (Example 3).

Mannitol and H-type H-USY (Si/Al=40, Zeolyst International, CBV-780) were mixed in a reaction container to carry out reaction. The weight of H-USY was 28% of the weight of mannitol. The container was heated to 150° C., and the dehydration reaction was carried out for 4 hours. Samples were taken from the reaction mixture at regular intervals, and the mannitol, 2,5-sorbitan, 1,4-mannitan and isomannide were analyzed. The results are shown in FIG. 4. The mannitol concentration steadily decreased as a function of time and, after about 60 minutes, it approached almost 0. At the same time, the sorbitan concentration steadily increased and, after about 30 minutes, exhibited a maximum value of 56%, the yield thereafter gradually decreasing. This suggests that 2,5 sorbitan was converted into other components. The 1,4-mannitan concentration increased early but, after one hour, it approached almost 10%. Correspondingly, the amount of isomannide produced early was small, but it increased as the amount of 1,4-mannitan decreased and, after about one hour, exhibited a maximum value of 22%.

Example 4

Figure 5:
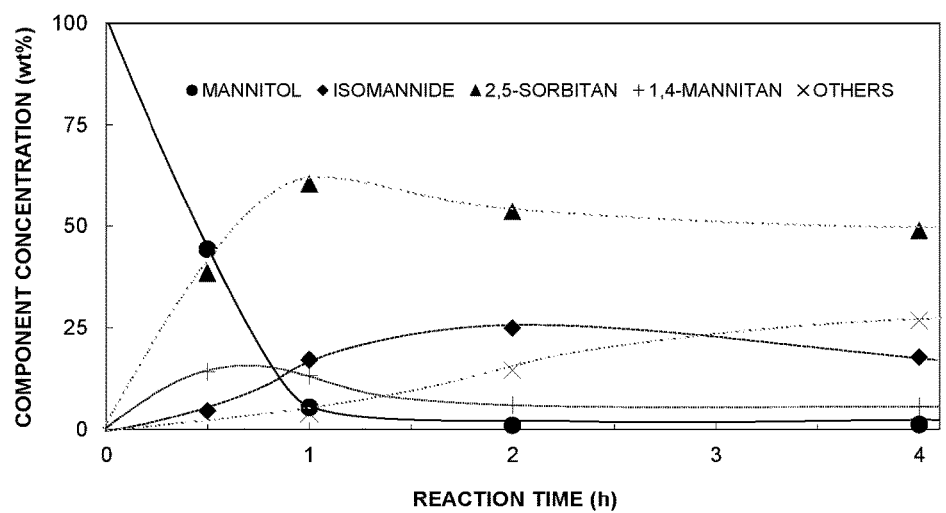
FIG. 5 shows results of analyses of mannitol, 2,5-sorbitan, 1,4-mannitan and isomannide, the results being obtained when a dehydration reaction (140° C.) of mannitol was carried out using H-type H-USY zeolite (Si/Al=40) (Example 4).

The reaction was carried out in the same manner as in Example 3, except that the reaction temperature was changed to 140° C. The results are shown in FIG. 5. The mannitol concentration steadily decreased as a function of time and, after about 60 minutes, it reached almost 0. At the same time, 2,5-sorbitan was first condensed from mannitol and, after 60 minutes, it was produced in a maximum yield of 61%, the yield subsequently decreasing a little, and after 4 hours, it became about 55%. The 1,4-mannitan concentration increased a little at first, then it decreased, and after one hour, it became almost 10%. The isomannide concentration was low at first, but it increased as the 1,4-mannitan concentration decreased. After about 2 hours, the isomannide concentration reached 25% and was saturated.

Example 5

Mannitol and an H-type β zeolite (Si/Al=12.5, Clariant Catalysts (Japan) K.K., H-BEA-25) were mixed in a reaction container to carry out the reaction. The weight of β-zeolite was 28% of the charge weight of mannitol. The container was heated to 150° C., and the dehydration reaction was carried out for one hour. Samples were then taken from the reaction mixture, and the mannitol, 2,5-sorbitan, 1,4-mannitan and isomannide were analyzed. The results are shown in Table 1.

Examples 6 to 11

The reaction was carried out in the same manner as in Example 5 except that, instead of β-zeolite in Example 5, H-type β zeolites having Si/Al values of 19, 25, 50, 75, 150 and 250 (Zeolyst International CP814C, Clariant Catalysts H-BEA-50, Tosoh HSZ-960-HOA, Clariant Catalysts H-BEA-150, Zeolyst International CP811C-300 and Tosoh HSZ-980-HOA, respectively) were each used. The results are shown in Table 1.

Example 12

The reaction was carried out in the same manner as in Example 5 except that, instead of β-zeolite in Example 5, H-USY (Si/Al=40, Zeolyst International, CBV-780) was used as the zeolite. As a result, the conversion of mannitol was 98%, the yield of isomannide was 22%, the yield of 1,4-mannitan was 7%, and the yield of 2,5-sorbitan was 52%.

Comparative Example 1

The reaction was carried out in the same manner as in Example 5 except that, instead of β-zeolite in Example 5, sulfuric acid (normality: 36 N) was used in an amount of 0.43% of the weight of mannitol. The results are shown in Table 1.

Comparative Example 2

The reaction was carried out in the same manner as in Example 5 except that, instead of β-zeolite in Example 5, H-mordenite (Si/Al=45, Catalysis Society of Japan) was used. The results are shown in Table 1.

Comparative Example 3

The reaction was carried out in the same manner as in Example 5 except that, instead of β-zeolite in Example 5, a strongly acidic ion-exchange resin Nafion SAC-13 (SIGMA-ALDRICH) was used. The results are shown in Table 1.

Comparative Example 4

The reaction was carried out in the same manner as in Example 5 except that, instead of β-zeolite in Example 5, $SiO_2$—$Al_2O_3$ (Silica-alumina catalyst support, grade 135, SIGMA-ALDRICH) that was a typical solid acid catalyst was used. The results are shown in Table 1.

Comparative Example 5

The reaction was carried out in the same manner as in Example 5 except that, instead of β-zeolite in Example 5, H-ZSM-5 (Si/Al=45, Clariant Catalysts (Japan) K.K.) was used as the zeolite. The results are shown in Table 1.

The results of the above Examples 5 to 12 and Comparative Examples 1 to 5 are shown in Table 1.

TABLE 1

| | | | Yield = (product weight/starting material weight) × 100 | | | |
|---|---|---|---|---|---|---|
| Example | Catalyst | Conversion of mannitol % | Isomannide % | 1,4-Mannitan % | 2,5-Sorbitan % | Others % |
| Ex. 5 | β-Zeolite (Si/Al = 12.5) | 73.2 | 37.9 | 10.4 | 19.1 | 5.9 |
| Ex. 6 | β-Zeolite (Si/Al = 19) | 82.3 | 40 | 7.5 | 23.1 | 11.8 |
| Ex. 7 | β-Zeolite (Si/Al = 25) | 96.5 | 50.6 | 3.7 | 19.6 | 22.6 |
| Ex. 8 | β-Zeolite (Si/Al = 50) | 96.3 | 60.3 | 3 | 17.2 | 15.9 |
| Ex. 9 | β-Zeolite (Si/Al = 75) | 98.4 | 60 | 3.1 | 14.3 | 21 |
| Ex. 10 | β-Zeolite (Si/Al = 150) | 96.8 | 52.2 | 4.6 | 22.2 | 17.8 |
| Ex. 11 | β-Zeolite (Si/Al = 250) | 74.3 | 26.6 | 13.8 | 19.7 | 14.2 |
| Ex. 12 | H-USY (Si/Al = 40) | 96.9 | 22.1 | 6.5 | 51.7 | 8.1 |
| Comp. Ex. 1 | $H_2SO_4$ | 97.1 | 19.8 | 4.5 | 26.4 | 46.4 |
| Comp. Ex. 2 | H-Mordenite (Si/Al = 45) | 13.5 | 1.7 | 3.6 | 6.3 | 1.9 |
| Comp. Ex. 3 | Strongly acidic ion-exchange resin (Nafion SAC-13) | 98.0 | 28.2 | 3.1 | 18.8 | 47.9 |
| Comp. Ex. 4 | $SiO_2$—$Al_2O_3$ | 0.8 | 0 | 0 | 0 | 0.8 |
| Comp. Ex. 5 | H-ZSM-5 (Si/Al = 45) | 26.3 | 12.6 | 3 | 2.6 | 8.1 |

The understanding below can be obtained from Table 1.

(1) When zeolites that are a solid heterogeneous catalyst were compared with sulfuric acid (Comparative Example 1) that is a homogeneous catalyst, the sulfuric acid catalyst provided a mannitol conversion of a value close to 100%. Nevertheless, the yield of the desired substance (isomannide or sorbitan) was low, by-products other than the desired substance making up the majority. In contrast, when β-zeolites were used as the catalyst, the conversion of mannitol was likewise close to 100%, and a high yield of isomannide and a high selectivity of 60% or more were observed.

(2) Further, when properties were examined by changing the composition ratio of Si to Al (Si/Al ratio), said Si and Al being components of the zeolite, it was found that, in the case of a Si/Al ratio of 10 to 300, a good isomannide yield was achieved and, particularly in the case of a Si/Al ratio in the range of 25 to 150, more preferably in the range of 40 to 100, the yield of isomannide increased.

(3) Furthermore, when a Y-type zeolite was used as the zeolite catalyst (Example 12), it was shown that the yield of 2,5-sorbitan was a value as high as about 52%.

(4) It is understood that the phenomenon where the proportions of products vary markedly depending upon whether β-zeolite or Y-type zeolite is used, even if the starting material is the same, indicates that the stereostructure of the zeolite greatly contributes to reaction selectivity.

(5) The above results indicate that isomannide and/or 2,5-sorbitan can be selectively produced with the use of the same starting material (mannitol) in the same apparatus at almost the same temperature and pressure by changing the catalyst from β-type to Y-type (or changing the catalyst from Y-type to β-type) or by mixing β-type and Y-type. This indicates that a flexible production that meets various needs of customers is possible.

(6) In the present invention, by using the zeolite catalyst mentioned above (H-type β zeolites and/or Y-type zeolites), a yield of about 60% was achieved in about one hour at a mild temperature of around 150° C. and atmospheric pressure or a pressure close thereto. After the reaction, separation and removal of the catalyst are easy, as is the purification of 2,5-sorbitan and isomannide because the products do not contain an acid or the like, and therefore, the productivity is high.

The invention claimed is:

1. A solid, dehydration catalyst for producing 2,5-sorbitan and/or isomannide from mannitol comprising an H-type β zeolite and/or a Y-type zeolite.

2. The solid, dehydration catalyst according to claim 1 consisting essentially of the H-type β-zeolite.

3. The solid, dehydration catalyst according to claim 1 consisting essentially of the Y-type zeolite.

4. The solid, dehydration catalyst according to claim 1, wherein the H-type β-zeolite and/or Y-type zeolite has a Si/Al atomic composition ratio of 10 to 300.

5. The solid, dehydration catalyst according to claim 4, wherein the Si/Al atomic composition ratio of the H-type β-zeolite and/or Y-type zeolite is 25 to 150.

6. The solid, dehydration catalyst according to claim 5, wherein the Si/Al atomic composition ratio of the H-type β-zeolite and/or Y-type zeolite is 40 to 100.

7. A process for producing 2,5-sorbitan and/or isomannide from mannitol, comprising the steps of:
   (a) adding the solid, dehydration catalyst according to claim 1 to mannitol to obtain a reaction mixture, and
   (b) heating the reaction mixture obtained in step (a) to a temperature of 110° C. to 170° C. at ambient pressure or under reduced pressure.

8. The process according to claim 7, wherein the amount of the solid, dehydration catalyst is 5 to 50% by weight, based on 100% by weight of the mannitol.

9. The process according to claim 7, wherein the solid, dehydration catalyst consists essentially of the H-type β zeolite, and wherein the process further comprises producing isomannide.

10. The process according to claim 7, wherein the process further comprises producing isomannide by 1,4-mannitan.

11. The process according to claim 7, wherein the solid, dehydration catalyst consists essentially of the Y-type zeolite, and wherein the process further comprises producing 2,5-sorbitan.

12. A process for selectively producing isomannide from mannitol or 2,5-sorbitan from mannitol comprising catalytically dehydrating mannitol by use of any of the compositions selected from the group consisting of an H-type β zeolite, a Y-type zeolite or a mixture thereof.

* * * * *